US011446311B2

(12) United States Patent
Fatholahi

(10) Patent No.: US 11,446,311 B2
(45) Date of Patent: *Sep. 20, 2022

(54) METHODS FOR TREATING PAIN ASSOCIATED WITH SICKLE CELL DISEASE

(71) Applicant: Shahin Fatholahi, King of Prussia, PA (US)

(72) Inventor: Shahin Fatholahi, King of Prussia, PA (US)

(73) Assignee: Shahin Fatholahi, King of Prussia, PA (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/934,131

(22) Filed: Jul. 21, 2020

(65) Prior Publication Data

US 2020/0345748 A1   Nov. 5, 2020

Related U.S. Application Data

(63) Continuation-in-part of application No. 16/124,957, filed on Sep. 7, 2018, now Pat. No. 10,736,874.

(60) Provisional application No. 62/555,861, filed on Sep. 8, 2017.

(51) Int. Cl.
*A61K 31/44* (2006.01)
*A61K 31/19* (2006.01)
*A61P 25/04* (2006.01)
*A61K 31/553* (2006.01)
*A61K 47/06* (2006.01)
*A61K 9/00* (2006.01)

(52) U.S. Cl.
CPC .......... *A61K 31/553* (2013.01); *A61K 9/0019* (2013.01); *A61K 47/06* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 2,909,462 A | 10/1959 | Warfield et al. |
| 3,133,132 A | 5/1964 | Sidney et al. |
| 3,173,876 A | 3/1965 | Zobrist |
| 3,276,586 A | 10/1966 | Rosaen |
| 3,541,005 A | 11/1970 | Baker et al. |
| 3,541,006 A | 11/1970 | Bixler et al. |
| 3,546,876 A | 12/1970 | Herman et al. |
| 3,830,803 A | 8/1974 | Draper et al. |
| 3,845,770 A | 11/1974 | Theeuwes et al. |
| 3,916,899 A | 11/1975 | Theeuwes et al. |
| 4,160,020 A | 7/1979 | Ayer et al. |
| 4,207,893 A | 6/1980 | Michaels |
| 4,327,725 A | 5/1982 | Cortese et al. |
| 4,855,294 A | 8/1989 | Patel et al. |
| 4,915,949 A | 4/1990 | Wong et al. |
| 5,002,776 A | 3/1991 | Geoghegan et al. |
| 5,051,260 A | 9/1991 | Chess et al. |
| 5,286,497 A | 2/1994 | Hendrickson et al. |
| 5,429,816 A | 7/1995 | Hofrichter et al. |
| 5,529,791 A | 6/1996 | Deboeck et al. |
| 5,552,136 A | 9/1996 | Motley |
| 5,643,588 A | 7/1997 | Roe et al. |
| 5,719,197 A | 2/1998 | Kanios et al. |
| 5,830,503 A | 11/1998 | Chen |
| 5,834,023 A | 11/1998 | Chen |
| 5,837,379 A | 11/1998 | Chen et al. |
| 5,965,163 A | 10/1999 | Miller et al. |
| 6,025,376 A | 2/2000 | Laurent et al. |
| 6,162,467 A | 12/2000 | Miller et al. |
| 6,270,805 B1 | 8/2001 | Chen et al. |
| 6,419,954 B1 | 7/2002 | Chu et al. |
| 6,524,620 B2 | 2/2003 | Chen et al. |
| 6,613,866 B2 | 9/2003 | Zofchak et al. |
| 6,638,528 B1 | 10/2003 | Kanios |
| 6,638,538 B1 | 10/2003 | Hashimoto et al. |
| 6,806,294 B2 | 10/2004 | Wimmer et al. |
| 6,923,984 B1 | 8/2005 | Remon |
| 6,946,120 B2 | 9/2005 | So et al. |
| 6,964,978 B2 | 11/2005 | Hageman et al. |
| 6,983,749 B2 | 1/2006 | Kumar et al. |
| 7,122,198 B1 | 10/2006 | Singh et al. |
| 7,399,488 B2 | 7/2008 | Hirsh et al. |
| 7,449,613 B2 | 11/2008 | Klofta et al. |
| 7,771,707 B2 | 8/2010 | Hirsh et al. |
| 7,776,345 B2 | 8/2010 | Dudhara et al. |
| 7,951,398 B2 | 5/2011 | Dietrich et al. |
| 8,012,496 B2 | 9/2011 | Dudhara et al. |
| 8,182,835 B2 | 5/2012 | Kim et al. |
| 8,377,474 B2 | 2/2013 | Hsu et al. |
| 8,383,152 B2 | 2/2013 | Jans et al. |
| 8,440,170 B2 | 5/2013 | Stroppolo et al. |

(Continued)

FOREIGN PATENT DOCUMENTS

| | | |
|---|---|---|
| EP | 0859766 | 5/2001 |
| EP | 1692118 | 4/2007 |

(Continued)

OTHER PUBLICATIONS

Kapfer et al., "Nefopam and Ketamine Comparably Enhance Post-Operative Analgesia," Anesth Analg. 100(1):169-174 (2005).
Lasseter et al., "Nefopam HCl Interaction Study with Eight Other Drugs," J Int Med Res 4:195-201 (1976).
Girard et al., "Nefopam Analgesia and its Role in Multimodal Analgesia: A Review of Preclinical and Clinical Studies," Clinical and Experimental Pharmacology and Physiology 43( 1): 3-12 (2016).
Ahmad et al., "Study of Pharmacokinetics and Comparative Bioavailability of Nefopam 30 mg Tablets in Twelve Fasting Healthy Pakistani Male Young Subjects: Single-Dose Randomized, Two-Period, Two-Treatment and Two-Way Cross-Over Design," Med. Princ. Pract. 21: 271-276 (2012).

(Continued)

Primary Examiner — Christine J Saoud
Assistant Examiner — Jon M Lockard
(74) Attorney, Agent, or Firm — Florek & Endres, PLLC

(57) ABSTRACT

A method for treating pain experienced by patients with sickle cell disease.

18 Claims, No Drawings

(56) References Cited

U.S. PATENT DOCUMENTS

| | | | |
|---|---|---|---|
| 8,461,171 B2 | 6/2013 | Holaday et al. |
| 8,513,304 B2 | 8/2013 | Kisak et al. |
| 8,575,211 B2 | 11/2013 | Girard et al. |
| 8,598,221 B2 | 12/2013 | Girard et al. |
| 8,834,921 B2 | 9/2014 | Kim et al. |
| 8,957,107 B2 | 2/2015 | Alman et al. |
| 9,044,398 B2 | 6/2015 | Hirsh et al. |
| 9,155,712 B2 | 10/2015 | Kanios et al. |
| 9,168,228 B2 | 10/2015 | Tygesen et al. |
| 9,205,052 B2 | 12/2015 | Kim et al. |
| 9,566,263 B2 | 2/2017 | Alman et al. |
| 2002/0165248 A1 | 11/2002 | Wimmer et al. |
| 2004/0081682 A1 | 4/2004 | Guenther et al. |
| 2006/0040905 A1 | 2/2006 | Lyne |
| 2006/0063753 A1 | 3/2006 | Bannister et al. |
| 2006/0160789 A1 | 7/2006 | Tirault et al. |
| 2007/0042969 A1 | 2/2007 | Rauschkolb-Loffler et al. |
| 2007/0043112 A1 | 2/2007 | Brew et al. |
| 2007/0043120 A1 | 2/2007 | Beyreuther et al. |
| 2007/0269379 A1 | 11/2007 | Mitragotri et al. |
| 2007/0276137 A1 | 11/2007 | James et al. |
| 2008/0031942 A1 | 2/2008 | Uchiyama et al. |
| 2008/0255079 A1 | 10/2008 | Lyne et al. |
| 2009/0215844 A1 | 8/2009 | Davis et al. |
| 2009/0227646 A1 | 9/2009 | Davis et al. |
| 2009/0263476 A1 | 10/2009 | Jobdevairakkam et al. |
| 2010/0152152 A1 | 6/2010 | Lyne et al. |
| 2010/0197777 A1 | 8/2010 | Girard et al. |
| 2011/0275626 A1 | 11/2011 | Perovitch et al. |
| 2011/0287094 A1 | 11/2011 | Penhasi et al. |
| 2014/0356428 A1 | 12/2014 | Barnscheid et al. |
| 2016/0310428 A1 | 10/2016 | Wening et al. |

FOREIGN PATENT DOCUMENTS

| | | |
|---|---|---|
| WO | 1997015561 | 5/1997 |
| WO | 2003105833 | 12/2003 |
| WO | 2005060957 | 7/2005 |
| WO | 2009053742 | 4/2009 |
| WO | 2014186581 | 11/2014 |

OTHER PUBLICATIONS

Wang et al., "Pharmacokinetics and Bioequivalence of Sustained-Release Tablet of Nefopam," Chinese Journal of Clinical Pharmacology and Therapeutics (2002).

Feng, S. "The Preparation of Nefopam Hydrochloride Sustained-Release Tablets and Its Drug Release in Vitro," Journal of Beijing Union University (Natural Sciences) (2006).

Wu et al., "Preparation of Nefopam Hydrochloride Controlled Porosity Osmotic Pump by Central Composite Design," Journal of Shenyang Pharmaceutical University (2009).

Singh et al., "Formulation, Optimization and Evaluation of Sustained Release Microspheres Using Taguchi Design." Journal of Pharmaceutical Technology, Research and Management, 2(1): 1-12 (2014).

Chu et al., "Characterization of Transdermal Delivery of Nefopam Hydrochloride Under Iontophoresis," Drug Development and Industrial Pharmacy, 20(18): 2775-2785 (1994).

Wilkinson et al., "A Double-Blind Comparison of Nefopam and Placebo Used as a Premedication in Children," Anaesthesia 39: 815-819 (1984).

Manoir et al., "Randomized Prospective Study of Analgesic Effect of Nefopam After Orthopaedic Surgery," British Journal of Anesthesia 91(6): 836-841 (2003).

Nam et al., "Effects of Nefopam on Streptozotocin-Induced Diabetic Neuropathic Pain in Rats," Korean J. Pain 27(4): 326-333 (2014).

Impax Laboratories, Inc., "Safety and Efficacy Study of IPX159 in Restless Legs Syndrome (RLS)", Retrieved from https://clinicaltrials.gov/ct2/show/NCT01521663?term=IPX 159&rank=1, (2013).

Reich et al., "Chapter 18: Tonicity, Osmoticity, Osmolality and Osmolarity," Remington: The Science and Practice of Pharmacy, 20th Ed., Lippincott Williams and Wilkins, Philadelphia, PA. pp. 246-262 (2000).

Remington, Science and Practice of Pharmacy 21st Edition, pp. 1000-1017 (2005).

United States Pharmacopeia 29 (2006) pp. 3257-3261.

Martindale, "Nefopam Hydrochloride," The Compete Drug Reference, 33rd ed. Pharmaceutical Press, (edited by S.C. Sweetman et al.) p. 62 (2002).

The Merck Index, "Nefopam," 13th ed. Merck Research Laboratories, (edited by M.J. O'Neil et al.), entry 6469 (2001).

British Pharmacopoeia, "Nefopam Hydrochloride, Analgesics Anti-inflammatory Drugs, and Antipyretics," 31 ed. p. 94 (2008).

Kim et al. "The Analgesic Efficacy and Safety of Nefopam in Patient-Controlled Analgesia after Cardiac Surgery: A Randomized, Double-Blind, Prospective Study," Journal of International Medical Research 42(3): 684-692 (2014).

Lee et al., "Nefopam vs Fentanyl in Female Patients Undergoing Laparoscopic Cholecystectomy," Enliven: J Anesthesiology and Critical Care Med. 1(3): May 26, 2014.

Yoon et al., "Post-Operative Intravenous Patient-Controlled Analgesic Efficacy of Morphine with Ketorolac Versus Nefopam after Laparoscopic Gynecologic Surgery: a Randomized Non-Inferiority Trial," Korean Journal of Anesthesiology (2016), 69 (2): 161-166.

Martinez et al., "Non-Opioid Analgesics in Adults after Major Surgery: Systematic Review with Network Meta-Analysis of Randomized Trials," British Journal of Anaesthesia (2017), 118 (1): 22-31.

Jin et al., "Opiod Sparing Effect and Safety of Nefopam in Patient Controlled Analgesia After Laparotomy: A Randomized, Double Blind Study," Journal of International Medical Research 44(3) 844-854, Apr. 2016.

Kapfer et al., "Nefopam and Ketamine Comparably Enhance PostoOerative Analgesia." Anesth. Analg. 100(1):169-174, Jan. 2005.

Moffat et al., "Postoperative Nefopam and Diclofenac: Evaluation of Their Morphine-Sparing Effect after Upper Abdominal Surgery," Anaesthesia, 1990, 45: 302-305.

Moon et al., "The Effect of Nefopam on Posteroperative Fentanyl Consumption: A Randomized, Double-blind Study," Korean Journal of Pain 29(2): 110-118, Apr. 2016.

Trop et al., "Comparison of Nefopam Hydrochloride and Propoxyphene Hydrochloride in the Treatment of Posteroperative Pain," Can. Anaesth. Soc. J., 26(4):296-304 Jul. 1979.

Laboureyras et al., "Long-Term Pain Vulnerability After Surgery in Rats: Prevention by Nefopam, an Analgesic with Antihyperalgesic Properties," Anesth. Analg., 109(2):623-31, Aug. 2009.

Buritova et al., "Effects of Nefopam on the Spinal Nociceptive Processes: a c-Fos Protein Study in the Rat," European Journal of Pharmacology 441:67-74 (2002).

Chawla et al., "Effect of Route of Administration on the Pharmacokinetic Behavior of Enantiomers of Nefopam and Desmethynefopam," Therapeutic Drug Monitoring 25:203-210 (2003).

Cho et al., "Antinociceptive Effect of Intrathecal Nefopam and Interaction with Morphine in Formalin-Induced Pain of Rats," Korean Journal of Pain 26:14-20 (2013).

Djerada et al., "Population Pharmacokinetics of Nefopam in Elderly, With or Without Renal Impairment, and its Link to Treatment Response," British Journal of Clinical Pharmacology 77:1027-1038 (2013).

Mimoz et al., "Nefopam Pharmacokinetics in Patients with End-Stage Renal Disease," Anesthesia and Analgesia 111:1146-1153 (2010).

Sanga et al. "Pharmacokinetics, Metabolism and Excretion of Nefopam, a Dual Reuptake Inhibitor in Healthy Male Volunteers," Xenobiotica 46:1001-1016 (2016).

Yu et al., "Pharmacokinetics, Distribution, Metabolism, and Excretion of the Dual Reuptake Inhibitor [14C]-Nefopam in Rats," Xenobiotica 46:1026-1048 (2016).

Zhang et al., "Comparison of the Effects of Nefopam and Tramadol on Postoperative Analgesia in Dogs Undergoing Ovariohysterectomy," Veterinami Medicina, 62, pp. 131-137 (2017).

(56) References Cited

OTHER PUBLICATIONS

Ahmad et al., "Study of Pharmacokinetics and Comparative Bioavailability of Nefopam 30 mg Tablets in Twelve Fasting Healthy Pakistani Male Young Subjects: Single-Dose, Randomized, Two-Period, Two-Treatment and Two-Way Cross-Over Design," Medical Principles and Practice, 21, pp. 271-276 (2012).

Cohen et al., "Nefopam Hydrochloride: New Analgesic Agent," J. Int. Med. Res., 4, pp. 138-143 (1976).

Bassett et al., "Studies on the Peripheral Pharmacology of Fenazoxine, a Potential Antidepressant Drug," Br. J. Pharmac., 37, pp. 69-78 (1969).

Bhatt et al., "Respiratory and Metabolic Effects of Oral Nefopam in Human Volunteers" Br. J. Pharmac., 11, pp. 209-211 (1981).

Aymard et al., "Comparative Pharmacokinetics and Pharmacodynamics of Intravenous and Oral Nefopam in Healthy Volunteers", Pharmacology and Toxicology 92: 279-286 (2003).

Eremenko, et al., "Combination of Nefopam and Ketoprofen for Analgesia can Minimize Opioids Use in the Early Period after Cardiovascular Surgery: 14AP8-6", European Journal of Anaesthesiology 31: 236 (2014).

Mimoz et al., "Analgesic Eficacy and Safety of Nefopam vs. Propacetamol Following Hepatic Resection", Anaesthesia 56: 520-525 (2001).

Kim et al., "Rediscovery of Nefopam for the Treatment of Neuropathic Pain," Korean Journal of Pain, vol. 27, No. 2, pp. 103-111, Apr. 2014.

Brandow et al., "Neuropathic Pain in Patients with Sickle Cell Disease," Pediatric Blood Cancer, 61, pp. 512-517, Oct. 26, 2013.

METHODS FOR TREATING PAIN ASSOCIATED WITH SICKLE CELL DISEASE

REFERENCE TO RELATED APPLICATIONS

This application is a continuation-in-part of U.S. patent application Ser. No. 16/124,957, filed on Sep. 7, 2018, now U.S. Pat. No. 10,736,874, which claims the benefits of U.S. Provisional Patent Application Ser. No. 62/555,861 filed on Sep. 8, 2017 and the contents of all of which are hereby incorporated by reference in their entireties into the present application.

FIELD OF THE INVENTION

The present invention relates to methods for treating pain associated with sickle cell disease. More specifically, the methods comprise the administration of nefopam, a nefopam metabolite, a nefopam prodrug, or isolated isomers thereof to treat pain associated with sickle cell disease.

BACKGROUND OF THE INVENTION

Sickle cell disease (hereinafter "SCD") is a genetic hematological disorder characterized by sickle-shaped red blood cells. SCD may result in arthralgia (joint pain), acute attacks of abdominal pain, pain in the hands and feet ("hand-foot syndrome"), long bone pain, ulceration of lower extremities, anemia, infections, and stroke. The symptoms of SCD may begin in childhood, sometimes as early as 6 months of age. SCD causes anemia. SCD may also lead to or be associated with other conditions such as vaso-occlusive crisis; splenic sequestration crisis; acute chest syndrome; aplastic crisis; or haemolytic crisis. Vaso-occlusive crisis is caused by the sickle-shaped red blood cells restricting or obstructing flow of blood to an organ and may produce pain and organ damage. Splenic sequestration crisis is the painful enlargement of the spleen caused by the trapping of red blood cells in the narrow vessels of the spleen.

The pain associated with the various manifestations of SCD has been treated with common over-the-counter pain medications such as aspirin, acetaminophen, and other non-steroidal anti-inflammatory agents (NSAIDs) such as ibuprofen, naproxen or diclofenac. In cases of more severe pain, opioids may be administered either orally or intravenously. Continued or prolonged administration of analgesics such as aspirin, acetaminophen, and NSAIDs may lead to gastrointestinal bleeding or ulcers, and some NSAIDs may lead to heart failure and stroke. Opioids are a class of drugs known to have strong analgesic effects in humans, however, opioids have numerous undesirable side effects such as itchiness, sedation, nausea, respiratory depression, constipation, and euphoria. Furthermore, continuous opioid use can lead to dependence often resulting in withdrawal syndrome. Moreover, because of the euphoric effects of opioids, recreational use is common and may lead to accidental overdose and death from respiratory depression. Currently, the United States is experiencing an increase in the rates of recreational use of opioids and addiction, which many attribute to the over-prescription of opioids for pain management.

Accordingly, there is a need for improved pain treatments for patients suffering from SCD that produces fewer side effects, does not produce respiratory depression, and has less abuse potential than opioids. Similarly, there is also a need for effective treatments of pain experienced by patients with SCD that allows for reduced doses of opioids and/or NSAIDs to thereby reduce the incidences of side effects and dependency.

SUMMARY OF THE INVENTION

The present invention provides a method for treating pain associated with SCD in human patients comprising the administration of nefopam, nefopam metabolite, nefopam prodrug, isolated isomers thereof, or combinations of the foregoing. The present invention also provides a method for treating pain associated with SCD comprising the administration of nefopam, nefopam metabolite, nefopam prodrug, isolated isomers thereof, or combinations of the foregoing in combination with one or more additional analgesics and/or opioids to thereby allow for a reduced dose of the one or more additional analgesics and/or opioids while still providing effective analgesia.

The present invention is directed generally to methods of treating pain associated with SCD in human patients comprising the administration of a therapeutic amount of nefopam, a nefopam metabolite, a nefopam prodrug, isolated isomers thereof, or combinations of the foregoing. The therapeutic amount of nefopam, nefopam metabolite, nefopam prodrug, isolated isomers thereof, or combinations of the foregoing, may be administered orally, parenterally, transdermally, transmucosally, or combinations thereof.

The methods of the present invention may further comprise the administration of one or more dosage forms or pharmaceutical compositions containing nefopam, nefopam metabolite, nefopam prodrug, isolated isomers thereof, or combinations of the foregoing, as the sole active ingredient. The dosage forms or pharmaceutical compositions may alternatively contain nefopam, nefopam metabolite, nefopam prodrug, isolated isomers thereof, or combinations of the foregoing, in combination with at least one additional analgesic, such as an opioid analgesic and/or NSAID in the same dosage form. The methods of the present invention also comprise the administration of one or more dosage forms or pharmaceutical compositions containing nefopam, nefopam metabolite, nefopam prodrug, isolated isomers thereof, or combinations of the foregoing as the sole active ingredient and the administration of a second dosage form or pharmaceutical composition comprising an opioid analgesic and/or NSAID. The administration of the second dosage form or pharmaceutical composition may be concurrently or sequentially to the administration of the one or more dosage forms containing the nefopam, nefopam metabolite, nefopam prodrug, isolated isomers thereof, or combinations of the foregoing, as the sole active ingredient.

In one embodiment of the present invention, the administration comprises the oral administration of a solid or liquid dosage form containing about 1 mg to about 1,000 mg, preferably about 5 mg to about 750 mg, and most preferably about 10 mg to about 500 mg of nefopam, nefopam metabolite, nefopam prodrug, isolated isomers thereof, or combinations of the foregoing. The oral administration may occur once, twice, three, four, five, or six times in a twenty-four hour period.

In another embodiment of the present invention, the administration comprises a parenteral administration of a dosage form or pharmaceutical composition, such as a subcutaneous, intravenous, intrathecal or intramuscular formulation, containing about 0.05 mg to about 250 mg of nefopam, nefopam metabolite, nefopam prodrug, isolated isomers thereof, or combinations of the foregoing. The parenteral administration may occur continuously, every four, six, eight, or ten hours, or on an as needed basis.

In a further embodiment of the present invention, the administration comprises a transdermal administration of a dosage form or pharmaceutical composition containing about 0.05 mg to about 500 mg of nefopam, nefopam metabolite, nefopam prodrug, isolated isomers thereof, or combinations of the foregoing. The transdermal administration may be in the form of an occluded dosage form such as a matrix or reservoir patch or an unoccluded dosage form such as a gel, cream, lotion, foam, or mousse comprising nefopam, nefopam metabolite, nefopam prodrug, isolated isomers thereof, or combinations of the foregoing applied to an SCD patient's outer skin surface. The transdermal administration may occur as once, twice, three, or four times daily or as needed. The transdermal administration may also allow for administration of an occluded dosage form once a day, every two, three, four, five, six, or seven days.

In a still further embodiment of the present invention, the administration comprises a transmucosal administration of a dosage form or pharmaceutical composition containing about 0.05 mg to about 500 mg of nefopam, nefopam metabolite, nefopam prodrug, isolated isomers thereof, or combinations of the foregoing. The transmucosal administration may be in the form of an orally disintegrating tablet, a sublingual or buccal tablet, an orally disintegrating film, or an oral spray for administration to an SCD patient's oral mucosa; a nasal spray for administration to an SCD patient's nasal mucosa; or a foam, spray, gel, or suppository for administration to the rectal, vaginal or urethral mucosa. The transmucosal administration may occur once, twice, three, four, five, or six times in a twenty-four hour period.

When the methods of the present invention include the administration in combination with a second analgesic such as an opioid analgesic and/or NSAID, the dose of the second analgesic may be reduced by about 5-95%, preferably about 20-75%, and most preferably about 50-70% of the normal dose of the second analgesic needed to provide pain relief in absence of the concomitant administration of the nefopam, nefopam metabolite, nefopam prodrug, isolated isomers thereof, or combinations of the foregoing.

The methods of the present invention are particularly useful in treating pain associated with vaso-occlusive crisis pain experienced by an SCD patient or pain associated with splenic sequestration crisis experienced by an SCD patient. In certain embodiments, the methods of the present invention are useful in treating joint pain, abdominal pain, pain in the hands, pain in the feet, long bone pain, or any combination of the foregoing pains experienced by an SCD patient.

DETAILED DESCRIPTION OF THE INVENTION

Except where noted, all terms are intended to have their normal meaning in the art, and are used as they would have been used by a person of ordinary skill at the time of the disclosure. It should be understood that throughout this application the singular forms, such as "a," "an," and "the," are often used for convenience, however, these singular forms are intended to encompass the plural unless otherwise specified, or unless the context clearly calls for the singular alone. It should also be understood that all publications, patents, books, journal articles, and the like, which are referred to in this application, are incorporated by reference in their entirety and for all purposes to the extent not inconsistent with the present disclosure.

"Nefopam" (also known as fenazoxine) refers to the chemical compound (RS)-5-methyl-1-phenyl-1,3,4,6-tetrahydro-2,5-benzoxazocine and has a CAS registry number of 13669-70-0. Nefopam has been known since the 1960's and its synthesis is described in U.S. Pat. No. 3,830,803. References to nefopam herein also include its pharmaceutically acceptable salts, such as nefopam hydrochloride, nefopam hydrobromide, nefopam tartrate, nefopam citrate, nefopam succinate, nefopam sulfate, nefopam phosphate, nefopam mesylate, and nefopam maleate. In certain embodiments, the nefopam may be administered as a racemic mixture, or as a pure or substantially pure, i.e., greater than 90%, preferably greater than 95%, and most preferably greater than 97%, of individual or isolated isomers, either the (R) or the (S) configuration.

"Nefopam metabolite" refers to any compound derived from a mammal's breakdown of nefopam following administration and absorption of nefopam. Representative examples include, but are not limited to, N-desmethyl nefopam and nefopam N-oxide. Unless otherwise indicated, the term "nefopam metabolite" refers to a compound that is isolated and purified outside of a mammal's body and incorporated into a pharmaceutical composition or dosage form for administration to a mammal, particularly humans, via any of the methods described herein. References to nefopam metabolite herein also include its pharmaceutically acceptable salts. In certain embodiments, the nefopam metabolite may be administered as a racemic mixture or as a pure or substantially pure, i.e., greater than 90%, preferably greater than 95%, and most preferably greater than 97%, of individual or isolated metabolite isomers, either the (R) or the (S) configuration.

"Nefopam prodrug" refers to any compound that includes the base nefopam structure but which has been modified to include a moiety which can be cleaved or removed by a mammal's, i.e., human's, metabolic system to produce the nefopam molecule or nefopam metabolite following administration of the nefopam prodrug to the mammal. Examples of nefopam prodrugs include, but are not limited to, derivatives of nefopam wherein the methyl moiety on the nitrogen is replaced with an ester, ether, hydroxy, alkoxy, or an alkyl moiety. Alternatively, the phenyl ring may be substituted with an ester moiety, ether moiety, hydroxyl moiety, alkoxy moiety, alkyl moiety or combination thereof. In the context of the term "nefopam prodrug" the term "alkyl" refers to a straight or branched hydrocarbon, preferably a $C_1$-$C_{12}$, except when the alkyl moiety is present on the nitrogen, then "alkyl" refers to a straight or branched hydrocarbon other than a methyl group. In certain embodiments, the nefopam prodrug is a compound wherein the methyl on the nitrogen has been replaced with a carboxylic acid ester moiety such as oxalic acid, malonic acid, malic acid, citric acid, tartaric acid, maleic acid, succinic acid, fumaric acid, glutamic acid, glutaric acid, adipic acid, pimelic acid, suberic acid, azelaic acid, sebacic acid, phthalic acid, isophthalic acid, and terephthalic acid. Representative examples of nefopam prodrug esters include, but are not limited to, 5-acetate-1-phenyl-1,3,4,6-tetrahydro-2,5-benzoxazocine, 5-ethanoate-1-phenyl-1,3,4,6-tetrahydro-2,5-benzoxazocine, 5-propionate-1-phenyl-1,3,4,6-tetrahydro-2,5-benzoxazocine, 5-butonate-1-phenyl-1,3,4,6-tetrahydro-2,5-benzoxazocine and individual isomers thereof. References to "nefopam prodrug" herein also include its pharmaceutically acceptable salts. In certain embodiments, the nefopam prodrug may be administered as a racemic mixture or as a pure or substantially pure, i.e., greater than 90%, preferably greater than 95%, and most preferably greater than 97%, of individual or isolated prodrug isomers, either the (R) or the (S) configuration.

"About" means having a value that is sufficiently close to the reference value so as to have identical or substantially identical properties as the reference value. Thus, depending on context, "about" can mean, for example, ±10%, ±9%, ±8%, ±7%, ±6, ±5%, ±4%, ±3%, ±2%, ±1%, or ±less than 1%.

"Pharmaceutically acceptable" refers to a material or method that can be used in medicine or pharmacy, including for veterinary purposes for example, in administration to a subject.

"Salt" and "pharmaceutically acceptable salt" includes both acid and base addition salts. "Acid addition salt" refers to those salts that retain the biological effectiveness and properties of the free bases, which are not biologically or otherwise undesirable, and which are formed with inorganic acids and organic acids. "Base addition salt" refers to those salts that retain the biological effectiveness and properties of the free acids, which are not biologically or otherwise undesirable, and which are prepared from addition of an inorganic base or an organic base to the free acid.

"Treating" includes ameliorating, mitigating, and reducing the instances of pain.

"Administering" includes any mode of administration, such as oral, subcutaneous, sublingual, transmucosal, parenteral, intravenous, intra-arterial, intrathecal, buccal, sublingual, topical, urethral, vaginal, rectal, ophthalmic, otic, nasal, inhaled, and transdermal. "Administering" can also include prescribing or filling a prescription for a dosage form comprising a particular compound. "Administering" can also include providing directions to carry out a method involving a particular compound or a dosage form comprising the compound.

"Administered in combination" and similar phrases as used herein means that nefopam, nefopam metabolite, nefopam prodrug, isolated isomers thereof, or combinations of the foregoing is administered with at least one additional pharmaceutically active compound or drug, preferably an opioid analgesic and/or NSAID. The nefopam, nefopam metabolite, nefopam prodrug, isolated isomers thereof, or combinations of the foregoing, and at least one additional pharmaceutically active compound, may be in the same dosage form, such as a tablet containing both pharmaceutically active compounds, or in separate dosage forms that are administered separately. In separate dosage forms, the administration of the separate dosage forms may occur at different times such as a few minutes apart, i.e., within 2-15 minutes, or longer, such as 1-6 hours.

"Effective amount" means the amount of nefopam, nefopam metabolite, nefopam prodrug, isolated isomers thereof, or combinations of the foregoing, when administered to a subject is sufficient to reduce or eliminate the pain. The therapeutically effective amount will vary depending on: the chemical identity and formulation form of the active substance; the particular type of pain and its severity; and the age, weight, and other relevant characteristics of the patient to be treated.

"Modified release" (also known as MR) includes delayed release (also known as DR) and controlled release (also known as CR, sustained release (SR), prolonged release (PR), or extended release (ER)).

"Delayed release" (also known as DR) relates to a pharmaceutical composition, dosage form, or component thereof that releases the active ingredients after a period of delay such as after one, two, or three hours. One type of DR dosage form is an enteric coated formulation that delays the release of the drug from the dosage form until the dosage form encounters an aqueous environment with a pH of 5 or greater.

"Controlled release" (also known as CR) refers to a pharmaceutical composition, dosage form, or component thereof that releases or delivers one or more pharmaceutical agents over a prolonged period of time, in this case over a period of more than one hour.

"Immediate release" (also known as instant release (IR)) refers to a pharmaceutical composition, dosage form, or component thereof which releases or delivers one or more pharmaceutical agents substantially immediately upon administration and will result in substantially complete dissolution within about one hour (or less), preferably less than 45 minutes, and most preferably in about 30 minutes or less when tested in a United States Pharmacopeia dissolution apparatus.

"Normal dose" of an opioid analgesic or NSAID means a dose of the opioid analgesic or NSAID that would be recommended for an SCD patient to take or a doctor would prescribe the SCD patient to take if the patient is not taking the opioid analgesic or NSAID in the same dosage form or in combination with nefopam, nefopam metabolite, nefopam prodrug, isolated isomers thereof, or combinations of the foregoing. In one aspect, normal doses of an opioid analgesic or NSAID are those doses that have been approved by the U.S. Federal Drug Administration for the particular drug when administered by a particular route. In another aspect, the normal dose of an opioid analgesic or NSAID is a dose that a patient has been taking prior to the initiation of the treatment in the same dosage form or in combination with nefopam, nefopam metabolite, nefopam prodrug, isolated isomers thereof, or combinations of the foregoing.

Pharmaceutical compositions or dosage forms that may be used in the methods of the present invention are described in Applicant's currently co-pending United States provisional and non-provisional patent applications, specifically, U.S. Provisional Patent Application Ser. No. 62/385,675 filed Sep. 9, 2016; U.S. Provisional Patent Application Ser. No. 62/463,355 filed Feb. 24, 2017; and U.S. Provisional Patent Application Ser. No. 62/464,218 filed Feb. 27, 2017; and U.S. Non-Provisional patent application Ser. No. 15/699,856 filed Sep. 8, 2017, the entireties of which are incorporated herein by reference.

One embodiment of the present invention comprises the oral administration of an immediate release solid or liquid dosage form comprising about 1 mg to about 500 mg, preferably about 5 mg to about 300 mg, and most preferably about 10 mg to about 200 mg of nefopam, nefopam metabolite, nefopam prodrug, isolated isomers thereof, or combinations of the foregoing. The immediate release solid or liquid dosage form is in the form of an immediate release tablet, capsule, powder, solution, or suspension that contains: nefopam or a pharmaceutically acceptable salt thereof such as nefopam hydrochloride or nefopam hydrobromide; a nefopam metabolite such as N-desmethyl nefopam or a pharmaceutically acceptable salt thereof or nefopam N-oxide or a pharmaceutically acceptable salt thereof; or a nefopam prodrug or a pharmaceutically acceptable salt thereof; and at least one pharmaceutically acceptable excipient such as a diluent, binder, glidant, lubricant, flavoring agent, pH adjusting agent, or combinations thereof. Examples of these pharmaceutically acceptable excipients are provided in Applicant's currently co-pending United States provisional patent applications and non-provisional patent applications, specifically, U.S. Provisional Patent Application Ser. No. 62/385,675 filed Sep. 9, 2016; U.S.

Provisional Patent Application Ser. No. 62/463,355 filed Feb. 24, 2017; U.S. Provisional Patent Application Ser. No. 62/464,218 filed Feb. 27, 2017; and U.S. Non-Provisional patent application Ser. No. 15/699,856 filed Sep. 8, 2017, the entireties of which are incorporated herein by reference, as well as, pages 3257-3261 of the United States Pharmacopeia 29 (2006) which are also incorporated herein by reference. The immediate release solid or liquid dosage form may be administered orally every four to six hours.

Another embodiment of the present invention comprises the oral administration of modified release solid or liquid dosage form comprising about 25 mg to about 1,000 mg, preferably about 50 mg to about 750 mg, and most preferably about 75 mg to about 500 mg of nefopam, nefopam metabolite, nefopam prodrug, isolated isomers thereof, or combinations of the foregoing. The modified release solid or liquid dosage form is in the form of a modified release tablet, capsule, powder, solution, or suspension that contains: nefopam, or a pharmaceutically acceptable salt thereof such as nefopam hydrochloride or nefopam hydrobromide; a nefopam metabolite such as N-desmethyl nefopam, or a pharmaceutically acceptable salt thereof, or nefopam N-oxide, or a pharmaceutically acceptable salt thereof; or a nefopam prodrug, or a pharmaceutically acceptable salt thereof; a rate controlling excipient; and at least one additional pharmaceutically acceptable excipient such as a diluent, binder, glidant, lubricant, flavoring agent, pH adjusting agent, or combinations thereof as previously described. The rate controlling excipient will control the release of the nefopam, nefopam metabolite, nefopam prodrug, isolated isomers thereof, or combinations of the foregoing from the modified release dosage form to provide therapeutic levels of nefopam or N-desmethyl nefopam for at least about 8 hours following oral administration of the modified release dosage form, at least about 12 hours following oral administration of the modified release dosage form, at least about 16 hours following oral administration of the modified release dosage form, at least about 20 hours following oral administration of the modified release dosage form, or at least about 24 hours following oral administration of the modified release dosage form. Examples of the rate controlling excipients are also provided in Applicant's currently co-pending United States provisional and non-provisional patent applications, specifically, U.S. Provisional Patent Application Ser. No. 62/385,675 filed Sep. 9, 2016; U.S. Provisional Patent Application Ser. No. 62/463,355 filed Feb. 24, 2017; U.S. Provisional Patent Application Ser. No. 62/464,218 filed Feb. 27, 2017; and U.S. Non-Provisional patent application Ser. No. 15/699,856 filed Sep. 8, 2017, the entireties of which are incorporated herein. The modified release solid or liquid dosage form may be administered orally every six, eight, twelve, sixteen, twenty, or twenty-four hours.

A further embodiment of the present invention comprises the parenteral administration, preferably subcutaneously, intramuscularly, intrathecally or intravenously, of about 1 mg to about 200 mg, preferably about 3.5 mg to about 100 mg and most preferably about 5 mg to about 75 mg of nefopam, nefopam metabolite, nefopam prodrug, isolated isomers thereof, or combinations of the foregoing. The parenteral dosage form when administered may be a solution or suspension that contains: nefopam or a pharmaceutically acceptable salt thereof such as nefopam hydrochloride or nefopam hydrobromide; nefopam metabolite such as N-desmethyl nefopam or a pharmaceutically acceptable salt thereof, or nefopam N-oxide or pharmaceutically acceptable salt thereof; or a nefopam prodrug or pharmaceutically acceptable salt thereof; and at least one pharmaceutically acceptable excipient such as a diluent, binder, glidant, lubricant, flavoring agent, pH adjusting agent, or combinations thereof as previously described. Examples of parenteral compositions used with the present invention can be found in U.S. Pat. Nos. 9,399,012; 8,722,679; 8,338,428; 7,612,102 and 6,992,218 which are incorporated herein by reference.

The parenteral administration may be administered, preferably intramuscularly or intravenously, every four to six hours or as needed. Alternatively, the parenteral administration may be a continuous intravenous administration.

The pharmaceutical composition for the parenteral administration may be presented in unit-dose or multi-dose containers, for example prefilled syringe, sealed vials, ampoules or intravenous bags. The pharmaceutical composition for parenteral administration ma) be provided in a sterile liquid form for administration or may be in a dry state, such as a powder, for example, a freeze dried (lyophilised) powder requiring only the addition of the sterile liquid carrier, for example, water prior to use.

In some embodiments, the pharmaceutical compositions for parenteral administration will comprise about 0.5 mg to about 100 mg of nefopam, nefopam metabolite, nefopam prodrug, isolated isomers thereof, or combinations of the foregoing, preferably about 2.5 mg to about 80 mg and most preferably about 5 mg to about 75 mg for single or unit dose compositions. The multi dose compositions will comprise 1000 mg or less of nefopam, nefopam metabolite, nefopam prodrug, isolated isomers thereof, or combinations of the foregoing, preferably 800 mg or less and most preferably 600 mg or less.

In some embodiments, the pharmaceutical compositions for parenteral administration may comprise at least one antioxidant. In some embodiments, the at least one antioxidant comprises cysteine hydrochloride monohydrate, thioglycolic acid thiolacetic acid, dithiothreitol, reduced glutathione, thiourea, alpha-thioglycerol, cysteine, acetylcysteine, or mercaptoethane sulfonic acid, ascorbic acid ascorbic acid derivatives, an organic compound having at least one thiol, an alkyl polyhydroxylated compound, or a cycloalkyl polyhydroxylated compound.

In some embodiments, the pharmaceutical composition for parenteral administration may comprises a buffering agent to maintain the pH of the liquid composition to be administered from about 4 to about 8, preferably about 4.5 to about 7.5 and most preferably about 5 to about 7. The buffering agent is a pharmaceutically acceptable salt or acid of citrate, phosphate, acetate, glutamate, tartrate, benzoate, lactate, histidine or other amino acids, gluconate, malate, succinate, formate, propionate, carbonate, or any combination thereof adjusted to an appropriate pH, as described herein, with acid (e.g., hydrochloric acid) or base (e.g., sodium hydroxide) as required.

In some embodiments, the pharmaceutical composition for parenteral administration has an osmolality from about 250 mOsm/L to about 400 mOsm/L when in solution. In some embodiments, the pharmaceutical composition further comprises an isotonicity agent. In some embodiments, the isotonicity agent is include, but are not limited to, mannitol, sorbitol, glycerol, sucrose, glucose, dextrose, levulose, fructose, lactose, polyethylene glycols 400 to 4000, phosphates, sodium chloride, potassium chloride, calcium chloride, calcium gluconoglucoheptonate, dimethyl sulfone or mixtures thereof.

In a further aspect provided herein the parenteral administration is repeated at least once with an interval of about 3 to about 5 hours. In some embodiments, the administration is repeated at least three, four, five or six times in a period of twenty four hours. In various embodiments, the parenteral administration is repeated three to eight times (e.g., 3 times, 4 times, five times, six times, seven times, or eight times) in a period of twenty four hours and about 15 mg to about 60 mg of nefopam, nefopam metabolite, nefopam prodrug, isolated isomers thereof, or combinations of the foregoing.

In some embodiments, the patient will initially receive one or two parenteral administrations to rapidly relieve the pain associate with sickle cell disease. One, two, three or four hours after the parenteral administration, the patient will receive oral doses of nefopam, nefopam metabolite, nefopam prodrug, isolated isomers thereof, or combinations of the foregoing as described herein, for 1-14 days, 1-7 days or 1-5 days.

Depending on the concentration of nefopam, nefopam metabolite, nefopam prodrug, isolated isomers thereof, or combinations of the foregoing in the parenteral formulation solution and consistent with the nefopam, nefopam metabolite, nefopam prodrug, isolated isomers thereof, or combinations of the foregoing dose levels described herein, the volume of parenteral formulation solution to be administered can vary from about 1 mL, to about 200 mL, e.g., 5 mL, 10 mL, 20 mL, 25 mL, 30 mL, 40 mL, 50 mL, 60 mL, 65 mL, 70 mL, 85 mL, 90 mL, 100 mL, 110 mL, 120 mL, 130 mL, 140 mL, 150 mL, 160 mL, 180 mL, or any other volume.

In some embodiments, the amount of time required for administration of the parenteral formulation and the intravenous formulation in particular ranges from about 10 seconds to about 1 hours, i.e., about 0.5 minutes, 1 minute, 2 minutes, 3 minutes, 4 minutes, 5 minutes, 10 minutes, 11 minutes, 15 minutes, 20 minutes, 30 minutes, 45 minutes, or any other administration time from about 1 minute to about 1 hour. In some embodiments, the amount of time required for administration of the IV formulation ranges from about 5 minutes to about 45 minutes, or about 5 minutes to about 30 minutes, or about 5 minutes to about 15 minutes.

A still further embodiment of the present invention comprises the transdermal administration of about 0.5 mg to about 500 mg, preferably about 2.5 mg to about 300 mg and most preferably about 5 mg to about 150 mg of nefopam, nefopam metabolite, nefopam prodrug, isolated isomers thereof, or combinations of the foregoing. The transdermal dosage form is administered by applying the dosage form or pharmaceutical composition that contains nefopam or a pharmaceutically acceptable salt thereof such as nefopam hydrochloride or nefopam hydrobromide, a nefopam metabolite such as N-desmethyl nefopam or a pharmaceutically acceptable salt thereof or nefopam N-oxide or pharmaceutically acceptable salt thereof, or a nefopam prodrug or pharmaceutically acceptable salt thereof, and at least one pharmaceutically acceptable excipient such as a diluent, binder, glidant, lubricant, flavoring agent, pH adjusting agent, or combinations thereof, as previously described, to the outer skin surface of an SCD patient. The preferred skin surfaces include thigh, abdomen, shoulder, arm, buttocks, or combination thereof for application of an occluded or unoccluded dosage form. The unoccluded dosage forms may also be applied directly to the area of pain such as a joint, hand, or foot. The transdermal administration may occur once, twice, three, or four times daily or as needed. The transdermal administration may also allow for administration of an occluded dosage form once a day, every two, three, four, five, six, or seven days.

A further embodiment of the present invention comprises the transmucosal administration of about 0.5 mg to about 500 mg, preferably about 2.5 mg to about 300 mg, and most preferably about 5 mg to about 150 mg of nefopam, nefopam metabolite, nefopam prodrug, isolated isomers thereof, or combinations of the foregoing. The transmucosal administration comprises the administration of a dosage form or pharmaceutical composition that contains nefopam or a pharmaceutically acceptable salt thereof such as nefopam hydrochloride or nefopam hydrobromide, a nefopam metabolite such as N-desmethyl nefopam or a pharmaceutically acceptable salt thereof or nefopam N-oxide or a pharmaceutically acceptable salt thereof, or a nefopam prodrug or a pharmaceutically acceptable salt thereof, and at least one pharmaceutically acceptable excipient such as a diluent, binder, glidant, lubricant, flavoring agent, pH adjusting agent, or combinations thereof, as previously described, and releases the nefopam, nefopam metabolite, nefopam prodrug, isolated isomers thereof, or combinations of the foregoing to the desired mucosal area. For example, the dosage form may be in the form of an orally disintegrating tablet, a sublingual, or buccal tablet, an orally disintegrating film, or an oral spray for administration of the nefopam, nefopam metabolite, nefopam prodrug, isolated isomers thereof, or combinations of the foregoing to an SCD patient's oral mucosa. The dosage form may be in the form of a nasal spray for administration of the nefopam, nefopam metabolite, nefopam prodrug, isolated isomers thereof, or combinations of the foregoing to an SCD patient's nasal mucosa. The dosage form may be in the form of a foam, spray, gel or suppository for administration of the nefopam, nefopam metabolite, nefopam prodrug, isolated isomers thereof, or combinations of the foregoing to an SCD patient's rectal, vaginal or urethral mucosa. The transmucosal administration may occur once, twice, three, four, five, or six times in a twenty-four hour period.

A further method of the present invention comprises the oral, parenteral, transdermal or transmucosal administration of nefopam, nefopam metabolite, nefopam prodrug, isolated isomers thereof, or combinations of the foregoing, as described above, in combination with a second analgesic. The second analgesic is preferably an NSAID or an opioid analgesic. The second analgesic may be in the same dosage form, i.e. tablet or capsule, as the nefopam, nefopam metabolite, nefopam prodrug, isolated isomers thereof, or combinations of the foregoing. Alternatively, the second analgesic may be in a separate and distinct dosage form from the nefopam, nefopam metabolite, nefopam prodrug, isolated isomers thereof, or combinations of the foregoing. If the second analgesic is in a separate and distinct dosage form, the dosage form containing the nefopam, nefopam metabolite, nefopam prodrug, isolated isomers thereof, or combinations of the foregoing, and the dosage form containing the second analgesic may be administered concurrently, preferably within about 0.25 to about 10 minutes of each other, or sequentially such as one, two, or three hours after administration of the first dosage form.

Examples of opioid analgesics suitable for use in the methods of the present invention include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl and derivatives, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papavereturn, pentazocine, phenadoxone, phenomorphan, phenazocine, phenoperidine, piminodine, piritramide, propheptazine, promedol, properidine, propoxyphene, sufentanil, tilidine, tramadol, pharmaceutically acceptable salts, complexes (e.g., with a cyclodextrin), stereoisomers, ethers, esters, hydrates, solvates, and mixtures thereof.

Preferably, the opioid analgesic is selected from the group consisting of codeine, hydrocodone, hydromorphone, morphine, oxycodone, oxymorphone, tramadol, pharmaceutically acceptable salts, complexes, stereoisomers, ethers, esters, hydrates, solvates, and mixtures thereof.

Examples of NSAIDs suitable for use in the methods of the present invention include, but are not limited to aspirin, acetaminophen, ibuprofen, flurbiprofen, ketoprofen, naproxen, oxaprozin, etodolac, indomethacin, ketorolac, lornoxicam, nabumetone, diclofenac, celecoxib, rofecoxib, meloxicam, piroxicam, valdecoxib, parecoxib, or etoricoxib, and combinations thereof. Preferred NSAIDs include, but are not limited to, acetaminophen, ketorolac, diclofenac, celecoxib, meloxicam, and combinations thereof.

The methods of the present invention which comprise the combined or sequential administration of nefopam, nefopam metabolite, nefopam prodrug, isolated isomers thereof, or combinations of the foregoing, with a second analgesic allows for a lower dose of the second analgesic and thereby alleviating some of the adverse events associated with the administration of NSAIDs and opioids. In a certain embodiment of the methods above, the dose of the second analgesic may be reduced by about 5-95%, preferably about 20-75%, and most preferably about 50-70% of the normal dose. For example, if the SCD patient is administered 20 mg of oxycodone every four hours, the methods of the present invention will reduce the amount of oxycodone administered to 2.5 mg to 10 mg every four hours. Similarly, if the SCD patient is administered 600 mg of naproxen every eight hours, the methods of the present invention will reduce the amount of naproxen administered to 150 mg to 400 mg every eight hours.

It is believed that the dosing regimens described in Table 1 will be useful in treating the pain associated with vaso-occlusive crisis or splenic sequestration crisis of SCD patients:

TABLE 1

| Drug | Dose | Form | Schedule |
|---|---|---|---|
| Nefopam hydrochloride | 5-100 mg | Immediate release tablet or capsule | Every 4-6 hours |
| N-desmethyl nefopam | 1-75 mg | Immediate release tablet or capsule | Every 4-6 hours |
| Nefopam hydrochloride | 10-250 mg | Controlled release tablet or capsule | Every 12-24 hours |
| N-desmethyl nefopam | 5-200 mg | Controlled release tablet or capsule | Every 12-24 hours |
| Nefopam hydrochloride | 0.5-75 mg | Intramuscular injection | Every 4-6 hours |
| N-desmethyl nefopam | 0.25-70 mg | Intramuscular injection | Every 4-6 hours |
| Nefopam hydrochloride | 0.5-60 mg | Intravenous injection | Every 4-6 hours |
| N-desmethyl nefopam | 0.25-50 mg | Intravenous injection | Every 4-6 hours |

It is further believed that the dosing regimens described in Table 1 can be used to treat joint pain, abdominal pain, pain in the hands, pain in the feet, long bone pain, or any combination of the foregoing pains experienced by an SCD patient.

It is also believed that the dosing regimens described in Table 1 can be used in combination with a second analgesic to reduce the amount of second analgesic administered to an SCD patient and still effectively treat the SCD patient's pain.

It is envisioned that any feature or element that is positively identified in this description may also be specifically excluded as a feature or element of an embodiment of the present invention as defined in the claims.

The invention described herein may be practiced in the absence of any element or elements, limitation or limitations which is not specifically disclosed herein. Thus, for example, in each instance herein, any of the terms "comprising," "consisting essentially of," and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A method for treating pain in a patient with sickle cell disease (SCD) comprising the parenteral administration of a therapeutic amount of nefopam, isolated isomers of nefopam, N-desmethyl nefopam, nefopam N-oxide, or combinations of the foregoing wherein the pain is due to vaso-occlusive crisis or splenic sequestration crisis.

2. The method of claim 1 wherein the pain is due to a vaso-occlusive crisis.

3. The method of claim 1 wherein the pain is due to splenic sequestration crisis.

4. The method of claim 1 wherein the administration comprises the parenteral administration comprising 0.5 to 100 mg of nefopam, isolated isomers of nefopam, N-desmethyl nefopam, nefopam N-oxide or combinations of the foregoing three, four, five or six times in a twenty-four hour period.

5. The method of claim 4 wherein the administration comprises intramuscular administration of about 0.5 mg to about 75 mg of nefopam, isolated isomers of nefopam, N-desmethyl nefopam, nefopam N-oxide or combinations of the foregoing.

6. The method of claim 4 wherein the administration comprises intravenous administration of about 0.5 mg to about 60 mg of nefopam, isolated isomers of nefopam, N-desmethyl nefopam, nefopam N-oxide or combinations of the foregoing.

7. The method of claim 1 further comprising the administration of a second analgesic.

8. The method of claim 7 wherein the second analgesic is an opioid.

9. The method of claim 7 wherein the second analgesic is a nonsteroidal anti-inflammatory agent (NSAID).

10. A method for treating pain in a patient with sickle cell disease (SCD) comprising the parenteral administration of a therapeutic amount of nefopam or a pharmaceutically acceptable salt thereof wherein the pain is due to vaso-occlusive crisis or splenic sequestration crisis.

11. The method of claim 10 wherein the pain is due to a vaso-occlusive crisis.

12. The method of claim 10 wherein the pain is due to splenic sequestration crisis.

13. The method of claim 10 wherein the administration comprises the parenteral administration comprising 0.5 to 100 mg of nefopam or a pharmaceutically acceptable salt thereof three, four, five or six times in a twenty-four hour period.

14. The method of claim 13 wherein the administration comprises intramuscular administration of about 0.5 mg to about 75 mg of nefopam or a pharmaceutically acceptable salt thereof.

15. The method of claim 13 wherein the administration comprises intravenous administration of about 0.5 mg to about 60 mg of nefopam or a pharmaceutically acceptable salt thereof.

16. The method of claim 10 further comprising the administration of a second analgesic.

17. The method of claim 16 wherein the second analgesic is an opioid.

18. The method of claim 16 wherein the second analgesic is a nonsteroidal anti-inflammatory agent (NSAID).

* * * * *